United States Patent
Nguyen et al.

(10) Patent No.: US 12,023,200 B2
(45) Date of Patent: Jul. 2, 2024

(54) SHEAR WAVE DETECTION OF ANATOMICAL VISCOSITY AND ASSOCIATED DEVICES, SYSTEMS, AND METHODS

(71) Applicant: KONINKLIJKE PHILIPS N.V., Eindhoven (NL)

(72) Inventors: Man Nguyen, Melrose, MA (US); Hua Xiwe, Cambridge, MA (US); Sheng-Wen Huang, Ossining, NY (US); Carolina Amador Carrascal, Everett, MA (US); Jean-Luc Francois Marie Robert, Cambridge, MA (US); Vijay Shamdasani, Kenmore, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 140 days.

(21) Appl. No.: 17/252,093

(22) PCT Filed: Jun. 26, 2019

(86) PCT No.: PCT/EP2019/067031
§ 371 (c)(1),
(2) Date: Dec. 14, 2020

(87) PCT Pub. No.: WO2020/002445
PCT Pub. Date: Jan. 2, 2020

(65) Prior Publication Data
US 2021/0251607 A1    Aug. 19, 2021

Related U.S. Application Data

(60) Provisional application No. 62/690,429, filed on Jun. 27, 2018.

(51) Int. Cl.
*A61B 8/00* (2006.01)
*A61B 8/08* (2006.01)

(52) U.S. Cl.
CPC .............. *A61B 8/485* (2013.01); *A61B 8/463* (2013.01); *A61B 8/5207* (2013.01)

(58) Field of Classification Search
CPC ....... A61B 8/485; A61B 8/463; A61B 8/5207; A61B 8/5223; A61B 8/54; G16H 50/30
See application file for complete search history.

(56) References Cited

U.S. PATENT DOCUMENTS 5,148,808 A * 9/1992 Satake .................. A61B 8/463
                                                  600/455
6,221,019 B1 * 4/2001 Kantorovich ........ A61B 8/4483
                                                  600/449

(Continued)

FOREIGN PATENT DOCUMENTS

JP    2017104526 A    6/2017
WO    2009140607 A1    11/2009

(Continued)

OTHER PUBLICATIONS

Zheng et al: "Detection of Tissue Harmonic Motion Induced by Ultrasonic Radiation Force Using Pulse-Echo Ultrasound and Kalman Filter"; IEEE Transactions on Ultrasonic, Ferroelectrics, and Frequency Control, vol. 534, No. 2, Feb. 2007, pp. 290-300.

(Continued)

*Primary Examiner* — Serkan Akar
*Assistant Examiner* — Gabriel Victor Popescu

(57) ABSTRACT

Systems, devices, and methods for performing ultrasound imaging are provided to advantageously determine the viscosity of an anatomy. According to one embodiment, a system for determining a viscosity of an anatomy includes an ultrasound transducer, a vibration source, and a processing system in communication with the ultrasound transducer and the vibration source. The processing system is configured to activate the vibration source to induce in the anatomy a first shear wave at a first frequency and a second shear (Continued)

wave at a second frequency, activate the ultrasound transducer to obtain ultrasound data representative of the anatomy that exhibits the first shear wave and the second shear wave, determine a first wave speed of the first shear wave and a second wave speed of the second shear wave, and determine the viscosity of the anatomy by comparing the first wave speed and the second wave speed.

11 Claims, 10 Drawing Sheets

(56) References Cited

U.S. PATENT DOCUMENTS

| | | |
|---|---|---|
| 2011/0137166 A1 | 6/2011 | Klee et al. |
| 2012/0065504 A1 | 3/2012 | Sandrin et al. |
| 2014/0371594 A1* | 12/2014 | Flynn ............... A61B 8/463 600/454 |
| 2015/0374338 A1 | 12/2015 | Sandrin et al. |
| 2017/0055836 A1* | 3/2017 | Thelen ............... A61B 5/4523 |
| 2017/0086780 A1* | 3/2017 | Sokulin ............... A61B 8/463 |
| 2017/0224304 A1* | 8/2017 | Sonoyama ............... A61B 8/463 |
| 2017/0258438 A1* | 9/2017 | Kanayama ............... A61B 8/463 |
| 2017/0333005 A1 | 11/2017 | Chen et al. |
| 2018/0000455 A1* | 1/2018 | Berkoff ............... A61B 8/463 |
| 2018/0098752 A1* | 4/2018 | Rouze ............... A61B 8/485 |

FOREIGN PATENT DOCUMENTS

| | | | | |
|---|---|---|---|---|
| WO | WO2009140607 A1 * | 11/2009 | ............... | A61B 5/08 |
| WO | WO 2018000103 A1 * | 1/2018 | ............... | A61B 8/461 |

OTHER PUBLICATIONS

PCT/EP2019/067031, ISR & WO, Oct. 8, 2019, 15 pages.
Sandrin et al: "Shear Modulus Imaging With 2-D Transient Elastography"; IEEE Transactions on Ultrasonics, Ferroelectrics, and Frequency Control, vol. 49, No. 4, Apr. 2002, pp. 425-435.
Sandrin et al: "Elasticity Probe for Soft Tissues With 1-D Transient Elastography"; IEEE Transactions on Ultrasonics, Ferroelectrics, and Frequency Control, vol. 49, No. 4, Apr. 2002, pp. 436 446.
Sandrin et al: "Time-Resolved Pulsed Elastography With Ultrafast Ultrasaonic Imaging"; Ultrasonic Imaging 21, pp. 259-272 (1999).

* cited by examiner

SHEAR WAVE DETECTION OF ANATOMICAL VISCOSITY AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2019/067031, filed on Jun. 26, 2019, which claims the benefit of U.S. Provisional Patent Application No. 62/690,249, filed on Jun. 27, 2018. These applications are hereby incorporated by reference herein.

TECHNICAL FIELD

The present disclosure relates generally to ultrasound systems and methods for determining the mechanical properties of an anatomy. For example, an ultrasound system can include an ultrasound imaging device and a vibration source configured to induce shear waves in the anatomy at one or more frequencies.

BACKGROUND

Many diseases result in growths, lesions, or other physical changes to organ tissue that can alter the tissue's mechanical properties. For example, a cancerous tumor may be stiffer than the surrounding healthy tissue. One way of assessing the stiffness or rigidity of a material is by determining or measuring the material's elasticity. In another example, a liver exhibiting steatosis may have increased fatty tissue in certain portions that exhibit a higher viscosity than other healthy portions of the liver.

Some of these mechanical property differences can be detected using ultrasound. For example, ultrasound elastography involves applying stress while measuring the resulting strain in tissue (strain imaging) and using ultrasound waves to induce shear waves in the anatomy, and detecting the characteristics of the wave propagating in the tissue of the anatomy and/or the effects of the wave on the anatomy. In shear wave elastography, an ultrasonic push-pulse induces a shear wave in the anatomy that propagates outward away from the push-pulse. The shear wave can be analyzed by an ultrasound transducer operating at a high frame rate to detect oscillatory displacement of the tissue caused by propagation of the shear wave through the tissue. By determining characteristics of the shear wave, such as its speed, at multiple locations in the tissue in the ultrasound image the elasticity of the tissue can be determined for each location.

Observing changes in elasticity is useful in detecting and diagnosing diseases in organs and tissue. However, some diseases, such as steatosis, may not exhibit the same changes in elasticity, but may manifest themselves by other mechanical characteristics, such as the tissue's viscosity.

SUMMARY

Systems, devices, and methods for performing ultrasound imaging are provided to advantageously determine the viscosity of an anatomy. For example, an ultrasound probe may include one or more vibration sources configured to induce a shear wave in the anatomy at different frequencies. Because the speed of the induced shear wave is partially dependent on the frequency of the shear wave and the viscosity of the anatomy, one way to determine the viscosity of the anatomy is to induce shear waves at different frequencies, and compare the speed of the shear waves at each frequency. A comparison of the speeds of the shear waves can be a measure or representation of the viscosity of the anatomy. This process can be performed for a plurality of points on an ultrasound image of the anatomy, such as a B-mode image, to create a visual depiction of the viscosity of the anatomy at each of the plurality of points. The visual depiction can then assist a physician in determining the presence and extent of one or more diseases detectable by viscosity measurements.

According to one embodiment of the present disclosure, a system for determining a viscosity of an anatomy includes an ultrasound transducer, a vibration source, and a processing system in communication with the ultrasound transducer and the vibration source. The processing system is configured to activate the vibration source to induce a first shear wave in the anatomy at a first frequency, activate the vibration source to induce a second shear wave in the anatomy at a second frequency, activate the ultrasound transducer to obtain ultrasound data representative of the anatomy that exhibits the first shear wave and the second shear wave, determine a first wave speed of the first shear wave in the anatomy and a second wave speed of the second shear wave in the anatomy, and determine the viscosity of the anatomy by comparing the first wave speed and the second wave speed.

According to some embodiments, the vibration source comprises a first vibrator and a second vibrator, and the processing system is configured to activate the first vibrator to induce the first shear wave, and activate the second vibrator to induce the second shear wave. In other embodiments, the processing system is configured to activate the first and second vibrators to alternatingly induce the first shear wave and the second shear wave. In still other embodiments, the vibration source comprises a first vibrator and a second vibrator, and the processing system is configured to activate the first and second vibrators to induce the first shear wave at a first time, and activate the first and second vibrators to induce the second shear wave at a second time.

In some embodiments, the processing system is configured to activate the vibration source to emit a broadband vibration comprising the first frequency and the second frequency, and apply a band pass filter to determine the first shear wave speed and the second shear wave speed. In some embodiments, the processing system is configured to apply a directional filter to the obtained ultrasound data. In other embodiments, the system further includes a user display in communication with the processing system, wherein the processing system is configured to determine a viscosity of the anatomy at a plurality of points in a field of view of the anatomy, generate, by the processing system, a visual depiction associated with the viscosity of the anatomy at each of the plurality of points in the field of view, and output the visual depiction to the user display. The processing system can be configured to activate the ultrasound transducer to obtain ultrasound imaging data of the anatomy, generate an ultrasound image of the anatomy based on the obtained ultrasound imaging data, and output, to the user display, the visual depiction overlaid on the ultrasound image. In some aspects, the visual depiction includes at least one of a plot associated with the first and second wave speeds or a map representative of the viscosity within the field of view. In other aspects, the processing system is configured to activate the vibration source to induce a third shear wave at a third frequency, determine a third wave speed of the third shear wave, and determine the viscosity of the anatomy by comparing the first wave speed, the second wave speed, and the third wave speed.

In another embodiment, a method for determining a viscosity of an anatomy includes inducing, by a vibration source, a first shear wave in the anatomy at a first frequency, inducing, by the vibration source, a second shear wave in the anatomy at a second frequency, obtaining, by an ultrasound transducer, ultrasound data representative of the anatomy that exhibits the first shear wave and the second shear wave, determining, by a processing system in communication with the vibration source and the ultrasound transducer, a first wave speed of the first shear wave in the anatomy and a second wave speed of the second shear wave in the anatomy based on the obtained ultrasound data, and determining, by the processing system, the viscosity of the anatomy by comparing the first wave speed and the second wave speed.

In some embodiments, the vibration source comprises a first vibrator and a second vibrator, and wherein inducing the first shear wave includes inducing the first shear wave using the first vibrator, and inducing the second shear wave includes inducing the second shear wave using the second vibrator. Inducing the first shear wave and inducing the second shear wave can include alternatingly inducing the first shear wave and the second shear wave by the first vibrator and the second vibrator. In some embodiments, the vibration source comprises a first vibrator and a second vibrator, and inducing the first shear wave and inducing the second shear wave includes inducing the first shear wave by the first vibrator and the second vibrator at a first time, and inducing the second shear wave by the first vibrator and the second vibrator at a second time.

In other embodiments, inducing the first shear wave and inducing the second shear wave includes emitting, by the vibration source, a broadband vibration including the first frequency and the second frequency, and determining the first wave speed and the second wave speed includes applying a band pass filter. In some aspects, the method further includes determining, by the processing system, a viscosity of the anatomy at a plurality of points in a field of view of the anatomy, and generating, by the processing system, a visual depiction associated with the viscosity of the anatomy at each of the plurality of points in the field of view. The method can further include obtaining, by the ultrasound transducer, ultrasound imaging data of the anatomy, generating, by the processing system, an ultrasound image of the anatomy based on the obtained ultrasound imaging data, and outputting, by the processing system to a user display, the visual depiction overlaid on the ultrasound image.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
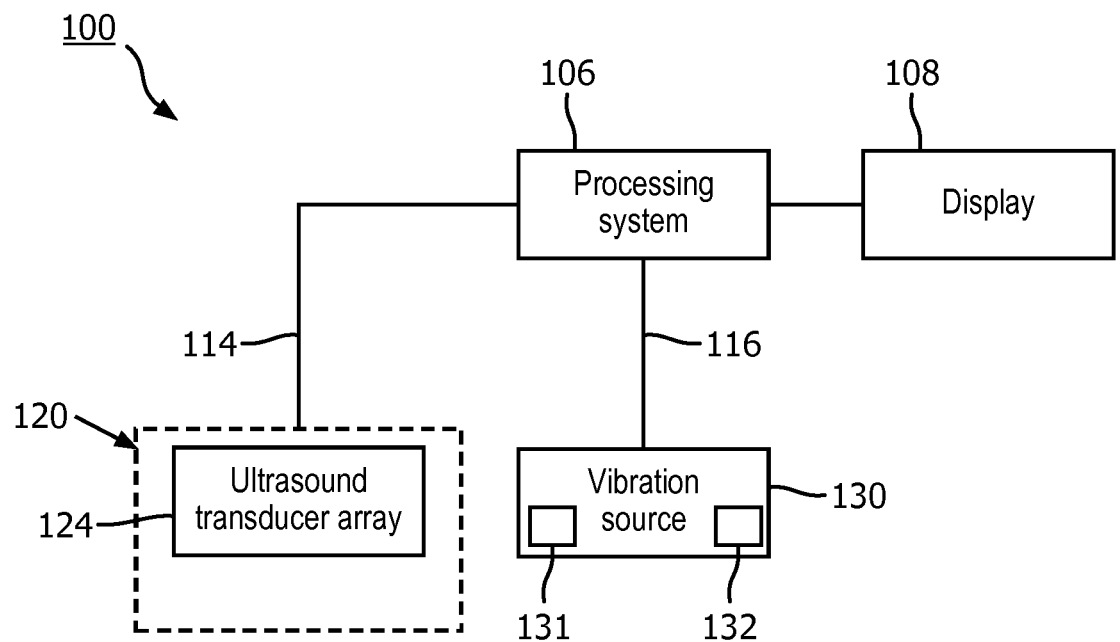
FIG. 1 is a diagrammatic schematic view of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound imaging system 100, according to aspects of the present disclosure. The ultrasound imaging system 100 may include an imaging device 120, a processing system 106, a user display 108, and a vibration source 130. The processing system 106 is in communication with the imaging device 120 and the user display 108 to control one or more aspects of the system 100. The ultrasound imaging system 100 may be any type of imaging system suitable for use in visualizing the tissue, organs, and anatomy of a patient. In some embodiments, the ultrasound imaging system 100 is a shear wave elastography imaging system. In some circumstances, the system 100 may include additional elements and/or may be implemented without one or more of the elements illustrated in FIG. 1.

In some embodiments, the imaging device 120 is sized and shaped to be placed on or near the anatomy of the subject to perform an ultrasound imaging procedure. The imaging device 120 may be placed directly on the body of the subject and/or adjacent the body of the subject. For example, the imaging device 120 may be directly in contact with the body of the subject while obtaining imaging data. In some embodiments, the device 120 includes one or more imaging elements which may be placed directly on or adjacent the body of the subject. In other embodiments, a housing of the imaging device is placed directly in contact with the body of the subject such that the imaging elements are adjacent the body of the subject. The subject may be a human patient or animal. The imaging device 120 may be portable and may be suitable to be used by a user in a medical setting. For example, the imaging device 120 may be a shear wave ultrasound imaging probe.

The imaging device 120 may include a transducer array 124. In some embodiments, a housing surrounds and protects the various components of the imaging device 120. In some embodiments, the housing is portable and may be sized and shaped for handheld grasping by an operator. The housing may be suitable for sterilization processes. The housing may include internal structure for securing the various components. For example, the transducer array may be placed in a compartment on a distal portion of the housing.

The transducer array 124 may include a number of transducer elements. These elements may be placed in a one-dimensional or two-dimensional array. In some embodiments, the transducer elements of the array 124 are configured to emit ultrasound signals and receive ultrasound echo signals corresponding to the emitted ultrasound signals. Transmit and receive data of the imaging device 120 and array 124 may be transmitted between the processing system and the imaging device 120 via a first communication line 114. For example, the received ultrasound echo signals may be transmitted by the first communication line 114 to the processing system 106 for processing.

The transducer array 124 may include a number of transducer elements. These elements may be arranged in a one-dimensional array, 1.x-dimensional array, such as a 1.5-dimensional array, or a two-dimensional array, in some instances. Any number of elements may be included in the ultrasound transducer assembly 120, for example, 1, 2, 4, 8, 16, 32, 64, 128, 256, 512, etc. The array 124 can be any suitable configuration, such as phased array including a planar array, a curved array, etc. The array 124 can be a matrix array, including one or more segments of ultrasound elements (e.g., one or more rows, one or more columns, and/or one or more orientations) that can be uniformly or independently controlled and activated. The imaging device 120 can include any suitable transducer type, including a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In some embodiments, the transducer elements of the array 124 are configured to emit ultrasound signals and receive ultrasound echo signals corresponding to the emitted ultrasound signals. In that regard, the ultrasound transducer or imaging device 120 can be configured obtain one-dimensional, two-dimensional, and/or three-dimensional images of the anatomy of the patient. The ultrasound echo signals may be stored in the memory and/or transmitted to the processing system 106 for further processing.

The device 120 may be used in combination with a vibration source 130 in communication with the processing system 106 via a second communication line 116. The vibration source 130 is configured to vibrate at various frequencies to induce vibrations or waves in the anatomy of the patient. For example, the vibration source 130 may be configured to induce shear waves in the anatomy at various frequencies. The vibration source 130 may comprise one or more vibrators, or vibrating elements, in some embodiments. In the embodiment illustrated in FIG. 1, the vibration source 130 includes a first vibrator 131, and a second vibrator 132. The first and/or second vibrator 131, 132 can comprise a variety of shapes including spherical (ball), bar, cylindrical, etc. Mechanical vibration sources for shear wave elastography have been described in, for example, U.S. Pat. No. 6,561,981 to Bonnefous et al., the entirety of which is hereby incorporated by reference. The first and second vibrators 131, 132 may be configured to vibrate simultaneously, or at different times. The vibration source 130 may comprise a separate component from the imaging device 120. In other embodiments, the vibration source 130 may be coupled to the imaging device 120 by a housing. For example, the housing may encapsulate the imaging device 120 and the vibration source 130 to form one integral component of the system 100. Although the vibration source 130 shown in FIG. 1 includes two vibrators 131, 132, it will be understood that the present disclosure contemplates embodiments that include fewer or more vibrators. For example, the vibration source 130 may comprise 1, 2, 3, 4, 5, or more vibrators.

Figure 2:
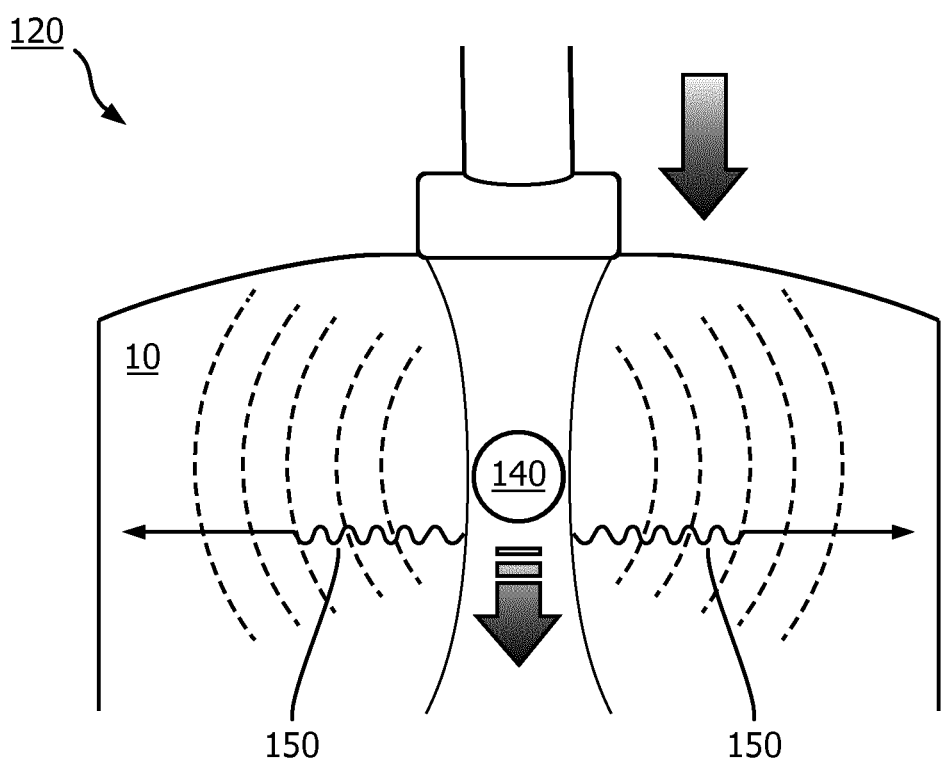
FIG. 2 is a diagrammatic view of a shear wave elastography ultrasound device inducing a shear wave in an anatomy, according to aspect of the present disclosure.

FIG. 2 shows a diagrammatic view of a shear wave elastography ultrasound device 120 inducing a shear wave 150 into the tissue 10, of a patient. To induce the shear wave 150, the device 120 directs a push-pulse 140 into the tissue 10. In the illustrated embodiment, the push-pulse 140 may be induced by an ultrasound transducer or transducer array, such as the array 124 depicted in FIG. 1. In other embodiments, the shear wave 150 may be induced by activating an external vibration source (e.g., FIG. 1, 130) to vibrate at one or more frequencies. The shear wave 150 can be a transverse wave or compression wave that displaces the tissue 10 in its trajectory. In the illustrated embodiment, the shear wave 150 may propagate spherically outward from a target of the push-pulse 140. In some embodiments, the shear wave 150 may propagate away from the device 120 and/or a vibration source 130. The device 120 can obtain ultrasound data from the tissue 10 exhibiting the shear wave 150 as it travels through the tissue 10. For example, by determining or measuring the velocity of the shear wave 150 at a plurality of locations in the tissue 10, the system 100 can determine the relative and/or absolute elasticity of the tissue 10 at each of the plurality of locations.

Figure 3:
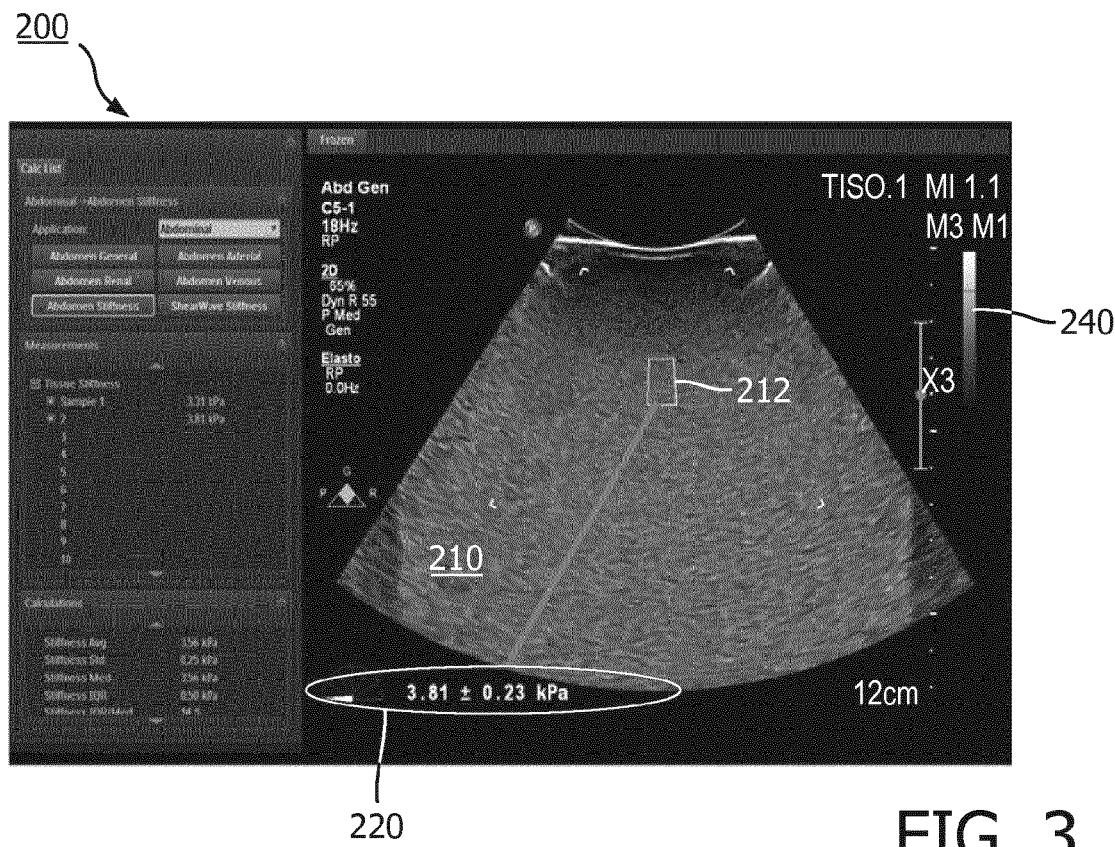
FIG. 3 is an exemplary illustration of a graphical interface of a shear wave elastography system, according to aspects of the present disclosure.

FIG. 3 shows a graphical user interface 200 of a shear wave elastography system, according to some embodiments. The graphical interface 200 can include an ultrasound image 210 of an anatomy, such as a B-mode image. Additionally, the interface 200 can display a visual depiction 220, such as a value, associated with the elasticity of the tissue at a selected location or region 212 on the image 210. The visual depiction 220 associated with the elasticity of the anatomy may vary depending on the selected location 212. For example, a physician may identify a feature in the B-mode image 210 that she wishes to inspect. By selecting a location associated with the identified feature, the physician can update the visual depiction 220 to indicate the elasticity of the tissue at the identified feature.

Figure 4:
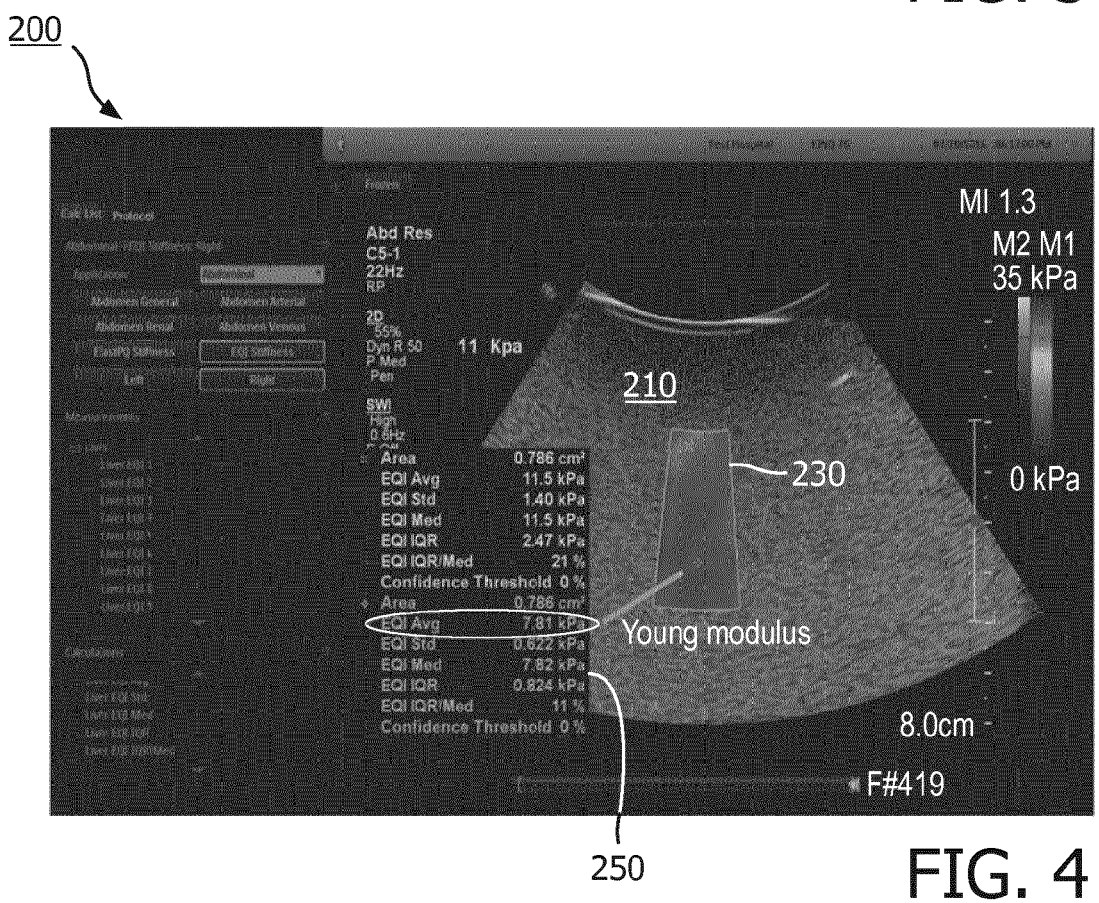
FIG. 4 is an exemplary illustration of a graphical interface of a shear wave elastography system, according to aspects of the present disclosure.

FIG. 4 shows the graphical user interface 200 of a shear wave elastography system, according to another embodiment. In the embodiment of FIG. 4, the graphical interface 200 can include a map 230 associated with the elasticity of the tissue at a plurality of points in a region of the anatomy. In the embodiment of FIG. 4, the map 230 is a two-dimensional visualization of the elasticity of the imaged anatomy overlaid on the B-mode image 210. In some embodiments, the map 230 comprises a confidence map and/or a heat map. The map 230 may represent elasticity values by various colors or hues. In some embodiments, an elasticity value may correspond to a particular color or hue. In other embodiments, a relative difference in elasticity may correspond to a particular color or hue. A legend 240 on the right side of the interface 200 shows the correlation between the color of a pixel or area of the map 230 and an elasticity value. In some embodiments, the map 230 may comprise a smaller or larger portion of the image 210. For example, in some embodiments, the map 230 may comprise substantially all of the image 210 such that the physician can observe the elasticity of the imaged anatomy at all points in the image 210. By contrast, a physician may choose to select only a small portion of the image 210 to overlay with the map 230. The interface 200 may also comprise an analytics panel 250 configured to display one or more characteristics of the image 210, system, and/or imaged anatomy. For example, the panel 250 can include various numerical values associated with the elasticity of the anatomy, the cross-sectional area of the anatomy associated with the map 230 in the image 210, and statistical calculations associated with the elasticity measurements. The embodiments depicted in FIGS. 3 and 4 represent elasticity by Young's modulus, measured in kilopascals (kPa). However, it is within the scope of the present disclosure to represent the elasticity of the anatomy by other moduli, measures, and/or values. For example, in some embodiments, the elasticity of the anatomy may be represented by a detected speed of the shear wave, measured in meters per second. In other embodiments, the elasticity may be represented by a dimensionless value, such as a proportion.

As discussed above, while elasticity is a useful characteristic in diagnosing various diseases, some diseases may not be as easily detected by observing elasticity. Some diseases may manifest themselves through other properties of the tissue, such as viscosity. For example, in steatosis, the liver accumulates fat in various regions of the liver tissue. The excess fat and other changes in the liver properties may be more readily identified by observing the viscosity of the liver. In some aspects, detecting shear waves and determining one or more aspects of the shear waves can also be used to determine the viscosity of the anatomy.

Figure 5:
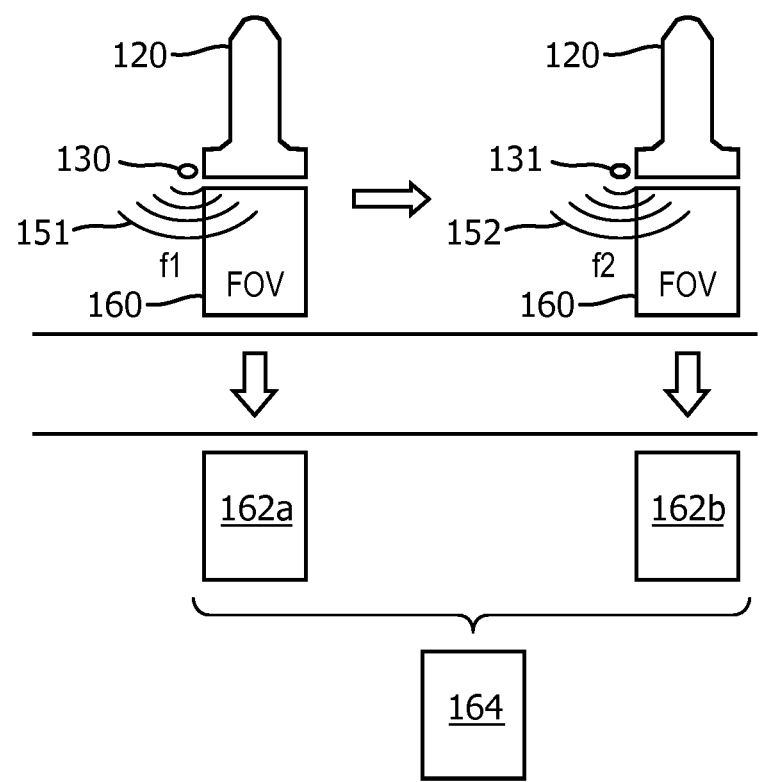
FIG. 5 is a diagrammatic view of an ultrasonic imaging system configured to determine the viscosity of an anatomy, according to aspects of the present disclosure.

FIG. 5 is an exemplary illustration of a shear wave ultrasound device 120 of a shear wave imaging system shown inducing a first shear wave 151 and a second shear wave 152 in an anatomy, according to embodiments of the present disclosure. The device 120 of FIG. 5 may be similar to the device of FIG. 1, in some aspects. For example, the device 120 of FIG. 5 comprises a vibration source 130. The first and second shear waves 151, 152 may be induced, or powered, by the vibration source 130. The vibration source 130 may be a separate component of the imaging system, or may be part of the device 120.

In some embodiments, the vibration source 130 comprises a mechanical vibrator or vibrating element. In other embodiments, the vibration source 130 may comprise an ultrasound transducer that induces shear waves by mechanically vibrating the whole transducer surface. In other embodiments, the shear waves can be generated by emitting a long push-pulse into the anatomy. The ultrasound transducer can be configured to obtain ultrasound imaging data of the anatomy in addition to tracking the propagation of the shear waves. In other embodiments, the vibration source 130 comprises both a mechanical vibrator and an ultrasound transducer, either of which can be used to accommodate different circumstances. For example, some areas of the anatomy may not be suited to facilitate propagation of a mechanical vibration, in which case the ultrasound transducer can be used to induce a shear wave in the anatomy. In some embodiments, the processing system 106 is configured to determine, based on imaging data, whether a mechanical vibration or an ultrasonic push-pulse should be used to induce the shear wave.

The vibration source 130 can be activated by the processing system to induce the first shear wave 151 at a first frequency f1. The first shear wave 151 may propagate through an area of the anatomy associated with a field of view 160 of the device 120. The field of view 160 can be the area of the anatomy that is imaged by an ultrasound transducer of the device 120. The field of view 160 may be imaged and represented by the ultrasound system 100 as a B-mode image. In some embodiments, the ultrasound system 100 is configured to obtain ultrasound data of the field of view 160 at a high frame rate. For example, the frame rate may be sufficiently high to observe the effects of the first shear wave 151 traveling through the field of view 160 in the anatomy.

By obtaining ultrasound data of the field of view 160 exhibiting the propagating first shear wave 151, the imaging system 100 can determine a first shear wave speed of the first shear wave 151 at a plurality of locations in the field of view 160. As explained further below with respect to FIGS. 6 and 7, the imaging system 100 may be configured to detect or determine the displacement of tissue caused by the first shear wave 151 as a function of time at a plurality of tracked positions within the field of view 160 to create a displacement plot for each of the tracked positions. If the distance between the tracked positions is known, the speed of the first shear wave 151 (and similarly, the second shear wave 152) can be obtained by, for example, comparing a plot of the displacement of the anatomy at a first tracked position to a plot of the displacement of the anatomy at a second tracked position. In some embodiments, a relative distance between the tracked positions is known, and in other embodiments, an absolute distance between the tracked positions is known. The imaging system 100 may then compile the first shear wave speed information associated with each of the plurality of locations in the field of view 160 (e.g., each pixel in the associated B-mode image) to generate a first map or plot 162a of the first shear wave speed in the field of view 160.

Next, the imaging system activates the vibration source 130 to induce a second shear wave 152 in the anatomy at a second frequency f2. The second frequency f2 can be different from the first frequency f1. In the illustrated embodiment, the second frequency f2 is shown to be greater than the first frequency f1. In other embodiments, the second frequency f2 can be less than the first frequency f1. The imaging system 100 can obtain high frame rate ultrasound data of the field of view 160 of the anatomy exhibiting the second shear wave 152. Based on the ultrasound data exhibiting the traveling second shear wave 152, the system can determine a second shear wave speed of the second shear wave 152 at a plurality of locations in the field of view 160. The plurality of locations associated with the second shear wave 152 may be identical to or associated with the plurality of locations for which data was obtained of the first shear wave 151. The system may then compile the shear wave speed information associated with the second shear wave 152 at each of the plurality of locations in the field of view to generate a second map or plot 162b of the second shear wave speed in the field of view 160. The first and second maps 162a, 162b may or may not be generated as visual depictions to be output to a display. In some embodiments, the first and second maps 162a 162b do not comprise visual depictions configured to be output to a display, but comprise data used by the processing system to generate other visual depictions, such as a viscosity map 164.

The viscosity map 164 can be generated by comparing the first map 162a to the second map 162b. For example, the viscosity map 164 can be created by subtracting the first map 162a from the second map 162b, or vice versa. In some embodiments, the viscosity map 164 is also normalized by the difference of the frequencies f1-f2, or vice versa. In other words, in some embodiments, the viscosity map 164 can be generated by analyzing the first and second shear wave speeds using the following relationship:

$$\eta = \frac{\Delta c_s}{\Delta f}$$

where $\eta$ represents an elasticity dispersion tissue property which assesses tissue viscosity, $\Delta c_s$ is the difference between the second shear wave speed and the first shear wave speed, and $\Delta f$ is the difference of the first frequency f1 and the second frequency f2, or vice versa. This relationship can be used to calculate the viscosity of the anatomy for each of a plurality of locations in the field of view 160 (e.g., each pixel in the B-mode image). By calculating the viscosity at each of the plurality of locations in the field of view 160, a viscosity map and/or a visual depiction can be generated to indicate the viscosity of the anatomy at each of the plurality of locations.

Figure 6:
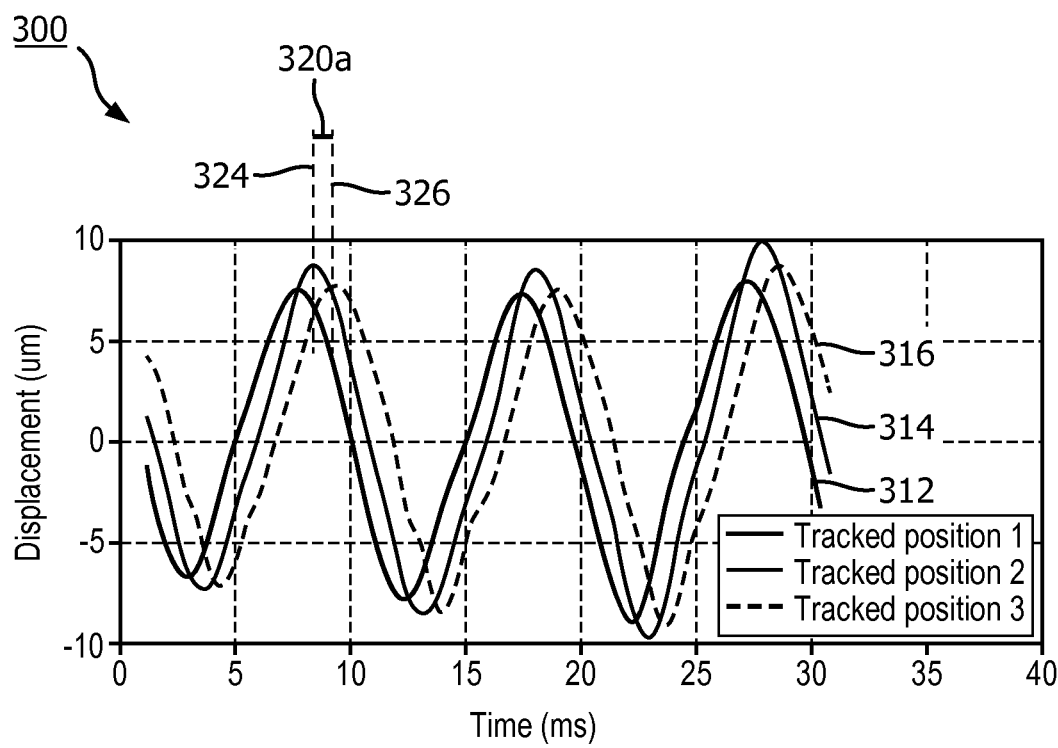
FIG. 6 is a graphical illustration of the viscosity- and frequency-dependent speed of a shear wave determined at a plurality of points in an anatomy.
Figure 7:
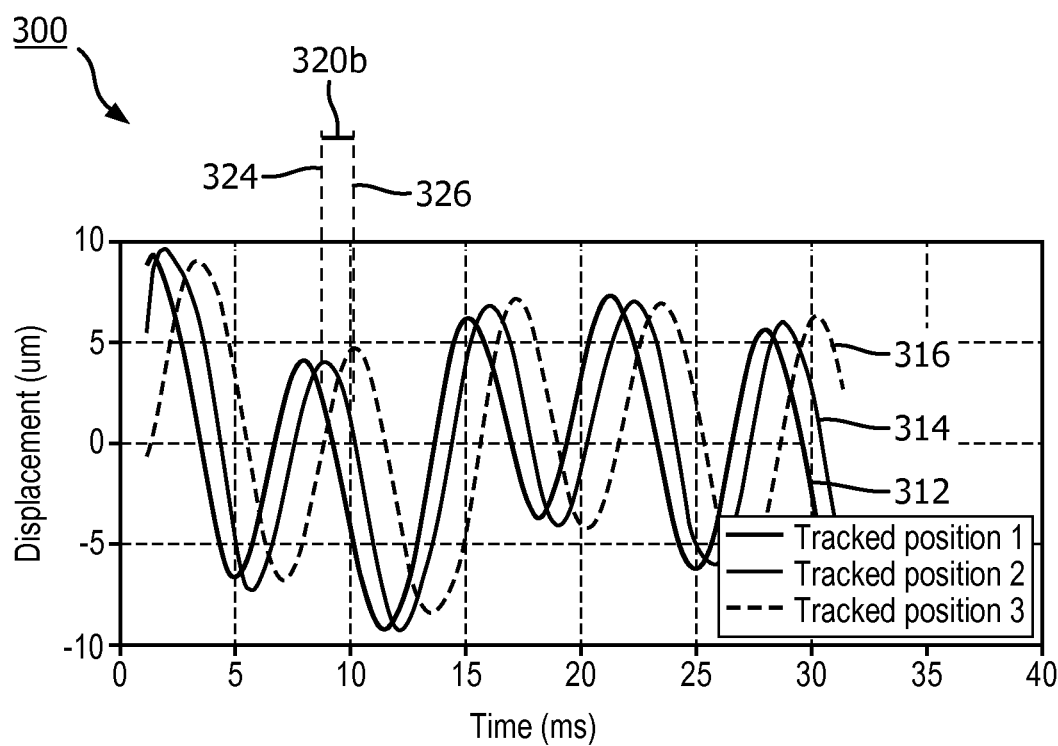
FIG. 7 is a graphical illustration of the viscosity- and frequency-dependent speed of a shear wave determined at a plurality of points in an anatomy.

FIGS. 6 and 7 depict graphs or plots of the displacement of the tissue or anatomy caused by the first shear wave 151 and the second shear wave 152, respectively. Referring to FIG. 6, the first shear wave 151 can be detected by a shear wave ultrasound system by detecting a displacement of tissue at each of a plurality of tracked positions, the displacement at each tracked position shown as a separate plot or curve. Thus, a separate plot 312, 314, 316 is created for each of tracked position 1, tracked position 2, and tracked position 3. The plots 312, 314, 316, are shown as having a wave or oscillating pattern, indicative of the of the first shear wave 151. Each of the plots 312, 314, 316 for tracked positions 1, 2, and 3, are spaced from one another, indicating a delay 320a of the first shear wave 151 traveling from tracked position 1, to tracked position 2, to tracked position 3. If the distance between tracked positions 1, 2, and 3 is known (e.g., absolutely or relatively), the first wave speed of the first shear wave 151 can be determined by the delay 320a, measured in milliseconds, of the first shear wave 151 traveling from tracked position 2 to tracked position 3, for example. The delay 320a may be determined by locating corresponding peaks 324, 326 of a second plot 314 associated with tracked position 2, and a third plot 316 associated with tracked position 3, respectively. For example, the known distance between tracked position 3 and tracked position 2 can be divided by the delay 320a between the location of peaks 326 and 324 to determine the first wave speed at the location between tracked position 2 and tracked position 3. This process can be repeated for each of a plurality of locations in the field of view to generate the first map 162a.

Referring now to FIG. 7, the graph 300 depicts the plots 312, 314, and 316, now showing the displacement of the second shear wave 152 at the second frequency C. In the depicted embodiment, the second frequency f2 of the second shear wave 152 represented by the graph 300 in FIG. 7 is greater than the first frequency f1 of the first shear wave 151 represented by the graph 300 in FIG. 6. The plots 312, 314, 316 of FIG. 7 can be compared similarly as discussed above with respect to FIG. 6. In that regard, a delay 320b can be calculated as the difference of the time position (i.e., time axis of the graph 300) of a third peak 326 and a second peak 324. It may be observed that the delay 320b between tracked positions 2 and 3 is greater than the delay 320a between the same tracked positions associated with the first shear wave 151 at the first frequency f1. In other words, the second shear wave speed associated with the second shear wave 152 is less than the first shear wave speed associated with the first shear wave 151. As discussed above with respect to FIG. 6, the process of determining a delay (e.g., 320b) for each of a plurality of locations in the field of view 160 where a distance between each of the plurality of locations is known, the system can generate the second map 162b showing the second wave speed at each of the plurality of locations on the second map 162b.

Although viscosity can be represented as the difference in wave speeds of a first and second shear wave, normalized by a difference in frequency, other formulas and relationships can also be used to determine viscosity based on one or more characteristics of a traveling shear wave. For example, shear wave speed and attenuation can indicate elasticity and viscosity of the medium (e.g., organs, tissue). Viscoelastic properties of a medium can be described by a complex shear modulus $G(\omega)$ defined by the relationship:

$$G(\omega) = G_s(\omega) + i * G_l(\omega)$$

where $G_s(\omega)$ is the storage modulus or elastic modulus and $G_s(\omega)$ is the loss modulus. Viscosity $\eta(\omega)$ can be defined as the ratio of loss modulus $G_l(\omega)$ to frequency. The shear wave speed $c_s(\omega)$ and attenuation $\alpha_s(\omega)$ are related to the complex shear modulus described above by the following relationships:

$$c_S(\omega) = \sqrt{\frac{2(G_s^2 + G_l^2)}{\rho(G_s + \sqrt{G_s^2 + G_l^2})}}$$

$$\alpha_S(\omega) = \sqrt{\frac{\rho\omega^2(\sqrt{G_s^2 + G_l^2} - G_s)}{2(G_s^2 + G_l^2)}}$$

where $\rho$ represents the density of the medium, and $G_s(\omega)$ and $G_l(\omega)$ are described above. Using these relationships and known properties of the anatomy, the viscoelastic properties of the anatomy can be determined. In some aspects, these relationships can be used to determine the elasticity and viscosity of the anatomy where only one shear wave is induced, and/or shear waves exhibiting a single frequency are used. The above relationships may facilitate a "model-free" approach to determining viscosity.

In still other aspects, one or more material models can be used to determine the elastic modulus and the loss modulus, and therefore the viscoelastic properties of the anatomy. Some common models, shown in the table below, include the Kelvin-Voigt model, the Maxwell model, and the Zener model:

| Model | $G_s(\omega)$ | $G_l(\omega)$ |
|---|---|---|
| Kelvin-Voigt | $\mu$ | $\omega\eta$ |
| Maxwell | $\dfrac{\mu\omega^2\eta^2}{\mu^2+\omega^2\eta^2}$ | $\dfrac{\mu^2\omega\eta}{\mu^2+\omega^2\eta^2}$ |
| Zener | $\dfrac{\mu_1\mu_2^2+\omega^2\eta^2(\mu_1+\mu_2)}{\mu_2^2+\omega^2\eta^2}$ | $\dfrac{\mu_2^2\omega\eta}{\mu_2^2+\omega^2\eta^2}$ | where $\mu$ is the elastic modulus, $\omega$ is the frequency of the shear wave, and $\eta$ is the viscosity. The above models can be used to translate a known elastic modulus $G_s$ and loss modulus $G_l$ into an approximation of elasticity and/or viscosity. In some embodiments, these models can be used to determine viscosity by determining the shear wave speed and attenuation of a shear wave at one frequency.

In some instances, it may be difficult or impractical to measure or determine one or more values or variables required by the relationships and models described above. For example, it may be impractical to reliably determine the attenuation of the shear wave, in some instances. It may be difficult to determine or approximate the density of the tissue. In that regard, the present disclosure includes methods, systems, and devices, to determine the viscosity of an anatomy by determining the difference in the speed of a shear wave at more than one frequency, and normalizing the difference in wave speed by the difference in frequency.

Figure 8:
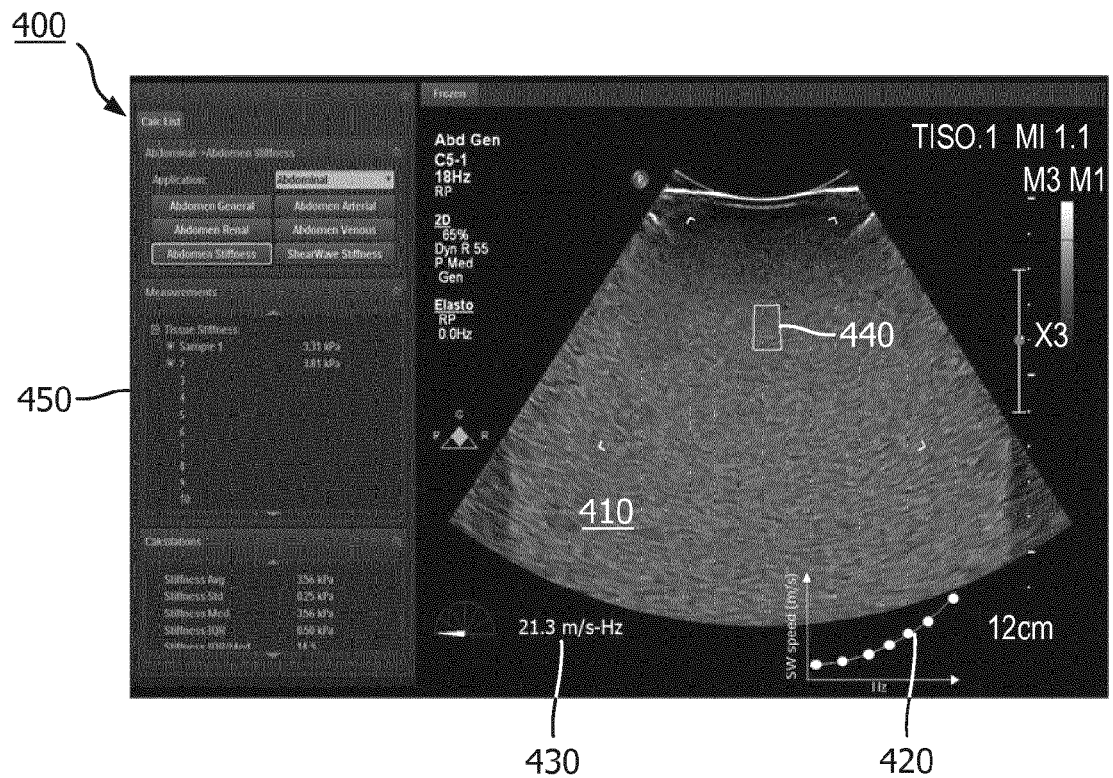
FIG. 8 is an exemplary illustration of a graphical interface of an ultrasonic system configured to determine the viscosity of an anatomy, according to aspects of the present disclosure.

FIG. 8 shows an exemplary embodiment of a graphical user interface 400 configured to indicate a viscosity of an anatomy associated with one or more locations on an ultrasound image 410. The interface 400 can include an ultrasound image 410 of an anatomy of a patient, such as the tissue of the patient. In some aspects, the image 410 can be a B-mode ultrasound image. The interface 400 can further include a viscosity plot 420 and a visual depiction 430. The interface 400 of the illustrated embodiment also comprises an analytics panel 450 configured to display one or more characteristics of the image 410, system 100, and/or imaged anatomy. For example, the panel 450 can include various numerical values associated with the elasticity and/or viscosity of the anatomy, the cross-sectional area of the anatomy associated with the visual depiction 430 and/or plot, and statistical calculations associated with the viscosity and/or elasticity measurements.

The plot 420 may depict wave speeds of a plurality of shear waves induced in the anatomy at different frequencies. In the illustrated embodiment, the plot 420 shows the wave speeds for seven shear waves induced at seven different frequencies. The individual points on the plot 420 may all be associated with one location on the image 410. The location may comprise a point, a line between two points, or an area of the image 410. For example, in some embodiments, the plot 420 may depict the average shear wave speeds of shear waves traveling through an area 440 demarcated by borders overlaid on the image 410.

In the embodiment of FIG. 8, the visual depiction 430 comprises a numerical value of the viscosity at a location on the image 410 in terms of shear wave speed normalized by frequency. In other embodiments, the visual depiction 430 may include numerical values associated with viscosity, such as poiseuille (PI), or Pascal-seconds. As described below, in some embodiments, the visual depiction 430 may comprise non-numerical indicators, such as plots, graphs, heat maps, or scales. The visual depiction 430 and plot 420 may be useful in analyzing the properties and features of the anatomy, for example, in the diagnosis of steatosis in the liver, or other diseases that affect the viscosity of the patient's organs and tissues.

Figure 9:
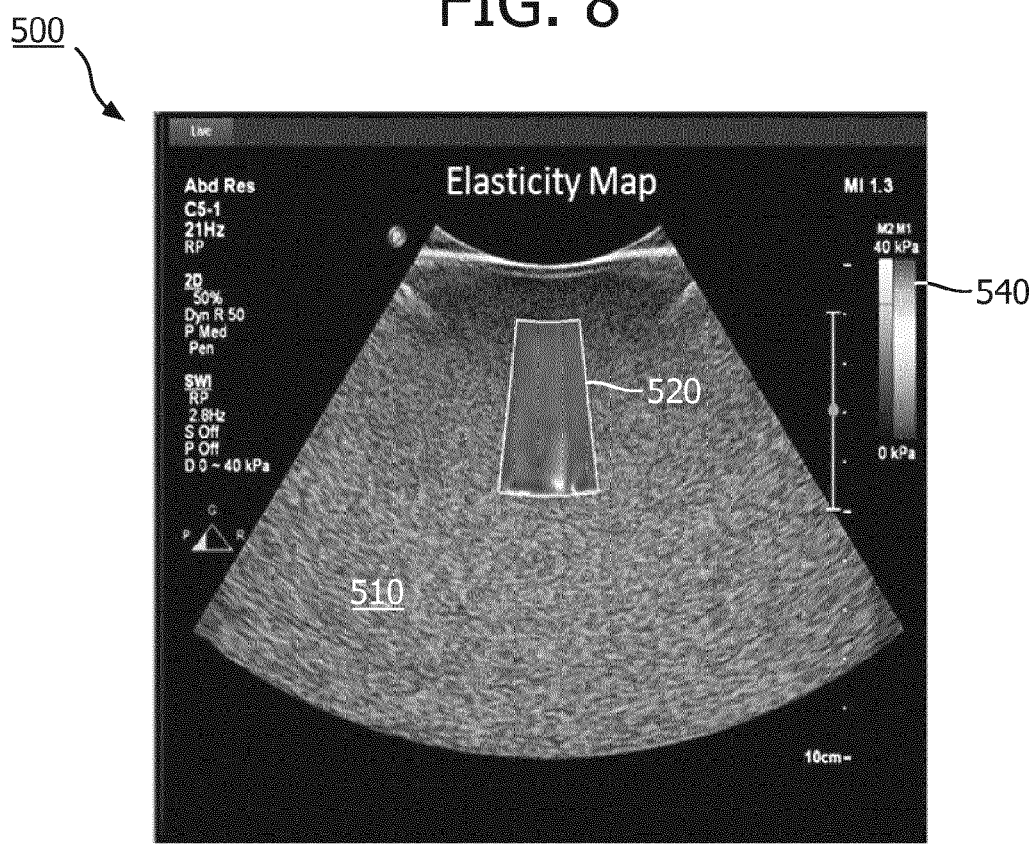
FIG. 9 is an exemplary illustration of a graphical interface of an ultrasonic system configured to determine the viscosity of an anatomy, according to aspects of the present disclosure.
Figure 10:
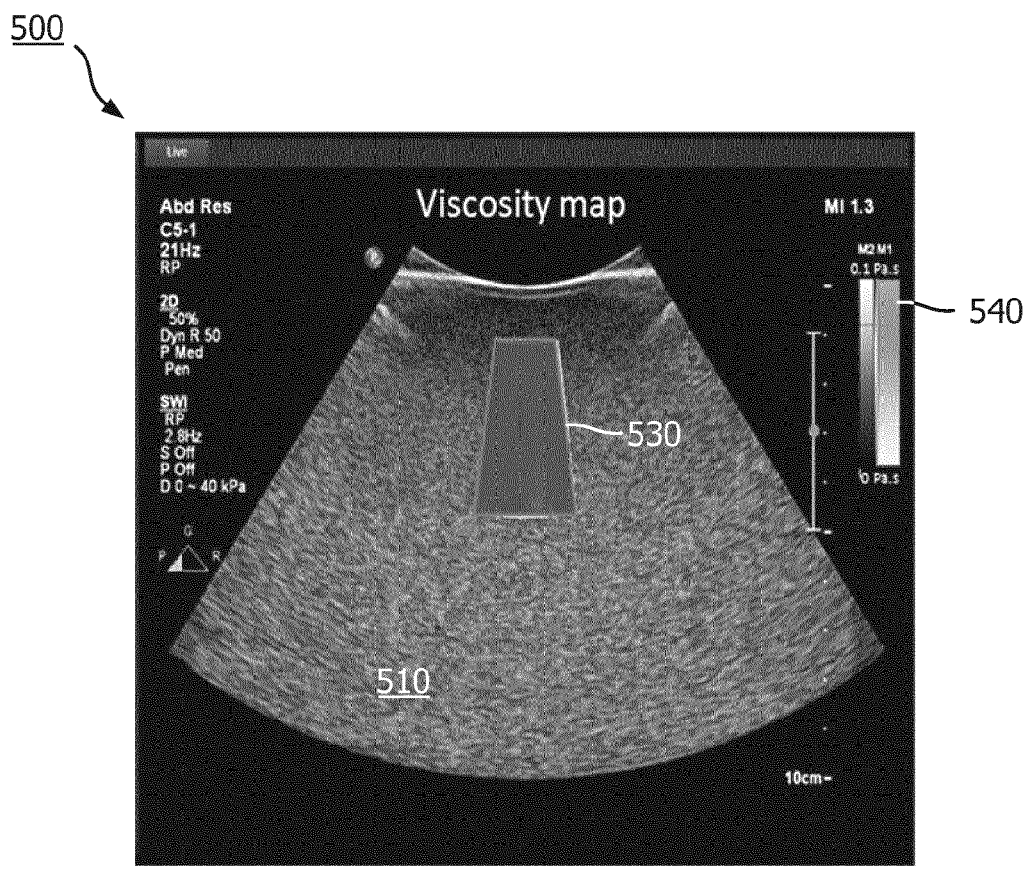
FIG. 10 is an exemplary illustration of a graphical interface of an ultrasonic system configured to determine the viscosity of an anatomy, according to aspects of the present disclosure.

FIGS. 9 and 10 show configurations of graphical user interfaces 500 displaying various properties of an anatomy. The interface 500 depicted in FIG. 9 includes an ultrasound image 510 of an anatomy, and a two-dimensional map 520 of the elasticity of a portion of the anatomy associated with an area of the image 510. The map 520 can be a heat map 520, in some instances. The heat map can assign and/or display various hues or colors associated with various elasticity values for each location represented in the map 520. For example, in some embodiments, each pixel included in the area of the map 520 is associated with an elasticity value, and a different color or hue is applied based on the elasticity values. A scale 540 on the right side of the interface 500 allows the physician to relate the colors in the map 520 to elasticity values. In some embodiments, the colors of the map 520 are associated with "absolute" elasticity values, such as Young's modulus. In other embodiments, the colors of the map 520 indicate relative elasticity values and are configured to indicate relative differences of elasticity of the tissue associated with the area of the map 520. In other embodiments, the colors of the map 520 indicate shear wave speeds at a certain frequency, for example 150 Hz.

Referring to FIG. 10, the interface 500 includes a viscosity map 530 overlaid on the image 510 that indicates a viscosity associated with a plurality of locations in the image 510. The map 530 may comprise and overlay a similar area of the image 510 overlaid by the map 520 in FIG. 9. Like the map 520 in FIG. 9, the map 530 may comprise a heat map configured to indicate values and/or differences in viscosity across the maps by applying a variety of colors or hues related to variety of viscosity values for each of a plurality of locations in the map 530. The scale 540 on the right side of the interface 500 can allow the physician to relate the colors or hues in the map 530 to viscosity values. In some embodiments, the colors of the map 530 are associated with "absolute" viscosity values, such as meters/second-Hz, or Pascal-seconds. In other embodiments, the colors of the map 530 indicate relative viscosity values of the anatomy associated with the area of the map 530.

In some embodiments, the maps 520 may overlay a larger or smaller portion of the image 510. For example, in some embodiments, the maps 520, 530 may overlay the entirety of the image 510. In other embodiments, the maps 520, 530 may overlay a relatively small area of the image 510. In some embodiments, the interfaces 500 of FIGS. 9 and 10 may be combined into a single interface. For example, the interfaces 500 may be displayed side-by-side. In other embodiments, the interfaces 500 are shown in separate windows. In some embodiments, a user may toggle between the interface 500 of FIG. 9 and the interface 400 of FIG. 10.

Figure 11:
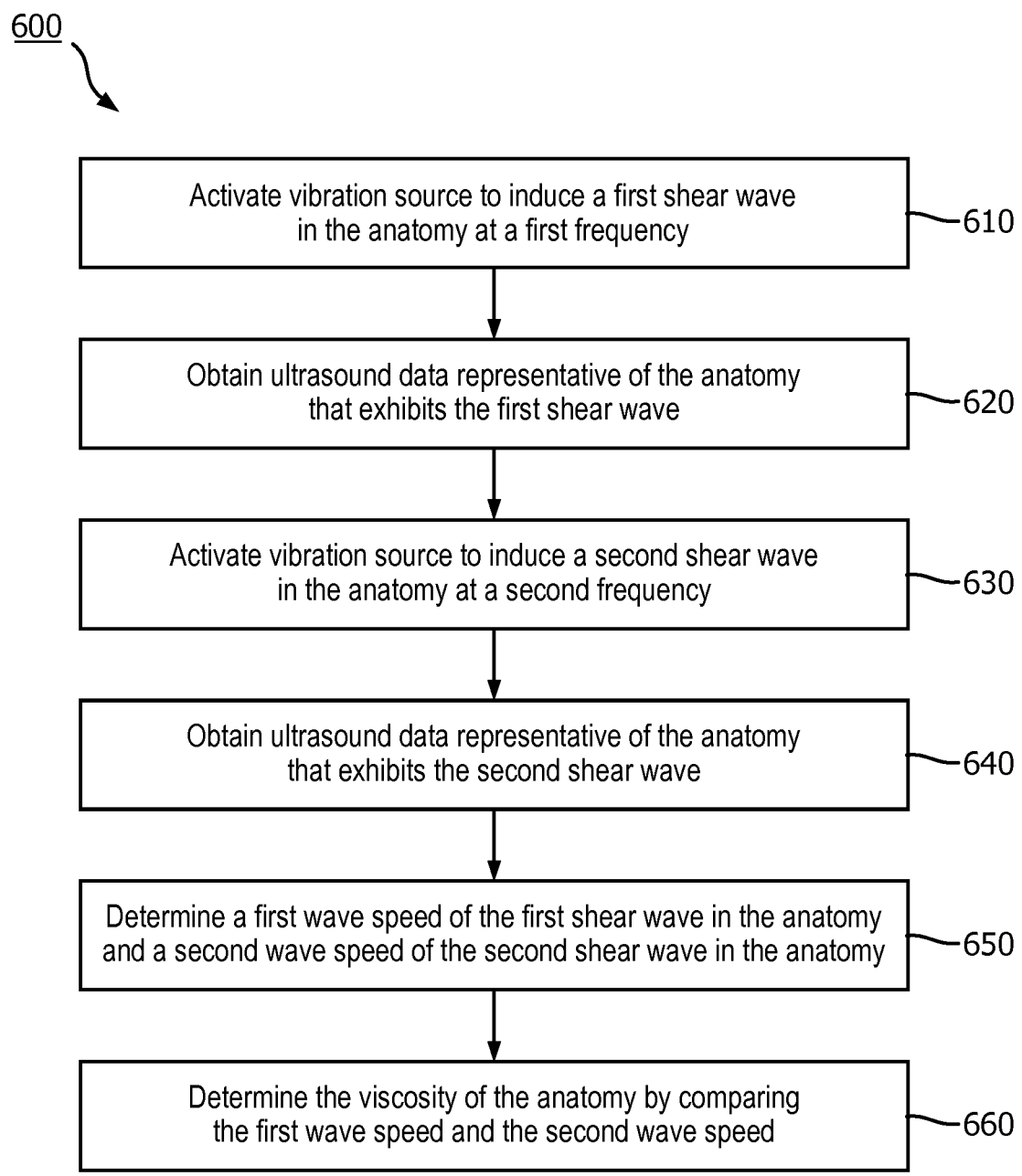
FIG. 11 is a diagrammatic view of a method for determining the viscosity of an anatomy, according to some aspects of the present disclosure.

FIG. 11 is a flow diagram of a method 600 for determining a viscosity of an anatomy, according to some embodiments. One or more steps of the method 600 may be performed and/or facilitated by a shear wave ultrasound imaging system, such as the system 100 shown in FIG. 1. In block 610, the system, via the processing system, activates a vibration source to induce a first shear wave in the anatomy at a first frequency. The first frequency may be any suitable frequency detectable by the system. In some embodiments, the frequency ranges from 50 Hz to 400 Hz. In one embodiment, the frequency may range from 100 Hz to 300 Hz. The vibration source can be configured to vibrate at the first frequency for one or more cycles, for example for 2-100 cycles.

In block 620, the system obtains ultrasound data representative of the anatomy that exhibits the first shear wave. In some instances, the ultrasound data may be ultrasound imaging data obtained by an external ultrasound probe. The obtained ultrasound data may be used to compile a B-mode image of the anatomy, in some instances. To detect the first shear wave propagating across the anatomy, the ultrasound data may be obtained at frame rate sufficiently high for the imaging system to determine a first wave speed of the first shear wave.

In block 630, the system, via the processing system, activates the vibration source to induce a second shear wave in the anatomy at a second frequency. The second frequency may lie in similar ranges as described above, such as 50 Hz to 400 Hz, and vibration source may vibrate at the second frequency for 2-100 cycles, for example, or continuously until the tracking stops, for example in 100 ms. In block 640, the system obtains ultrasound data representative of the anatomy that exhibits the second shear wave. As described above, the ultrasound data may be ultrasound imaging data obtained by an external ultrasound probe. The obtained ultrasound data may be used to compile a B-mode image of the anatomy, in some instances. To detect the second shear wave propagating across the anatomy, the ultrasound data may be obtained at frame rate sufficiently high for the imaging system to determine a first wave speed of the first shear wave.

Based on the obtained ultrasound data of the first and second shear waves, a first wave speed of the first shear wave and a second wave speed of the second shear wave are determined in block 650. The first and second wave speeds may be determined in accordance with the method described with respect to FIGS. 6 and 7. For example, the ultrasound data may indicate a displacement of the tissue or anatomy at one or more locations in the anatomy over time. As shown in FIGS. 6 and 7, the tissue displacement at a given location (e.g., tracked positions 1, 2, or 3) may exhibit a wave pattern in accordance with the first or second shear wave. By determining and comparing the delays of the first and second shear waves propagating through the anatomy from one location to another (e.g., tracked position 2 to tracked position 3), the imaging system can determine the first and second wave speeds of the first and second shear waves. In block 660, the wave speeds can be compared and normalized by the difference in the first frequency and second frequency to determine a viscosity, or a property of the anatomy representative of or associated with viscosity.

It will be understood that the method 600 may be performed in an order other than that depicted in FIG. 11. For example, in some embodiments, the imaging system may obtain ultrasound data of the anatomy exhibiting the first and second shear waves at the same time the first and second shear waves are induced. In some embodiments, the first and second shear waves may be induced simultaneously. For example, in one embodiment, the vibration source is configured to emit a broad band vibration where the multiple vibration frequencies are encoded in a long-duration vibration resulting in a shear wave exhibiting a wide range of frequencies, and the imaging system is configured to obtain ultrasound data of the anatomy exhibiting the broad band shear wave. By applying a band pass filter to the ultrasound data, the imaging system can identify a first shear wave, or a first component of the broadband shear wave, propagating at a first frequency (or first range of frequencies), and a second shear wave, or a second component of the broadband shear wave, propagating at a second frequency (or range of frequencies). The wave speeds of the first and second shear waves can be compared to determine the viscosity of the anatomy.

Figure 12:
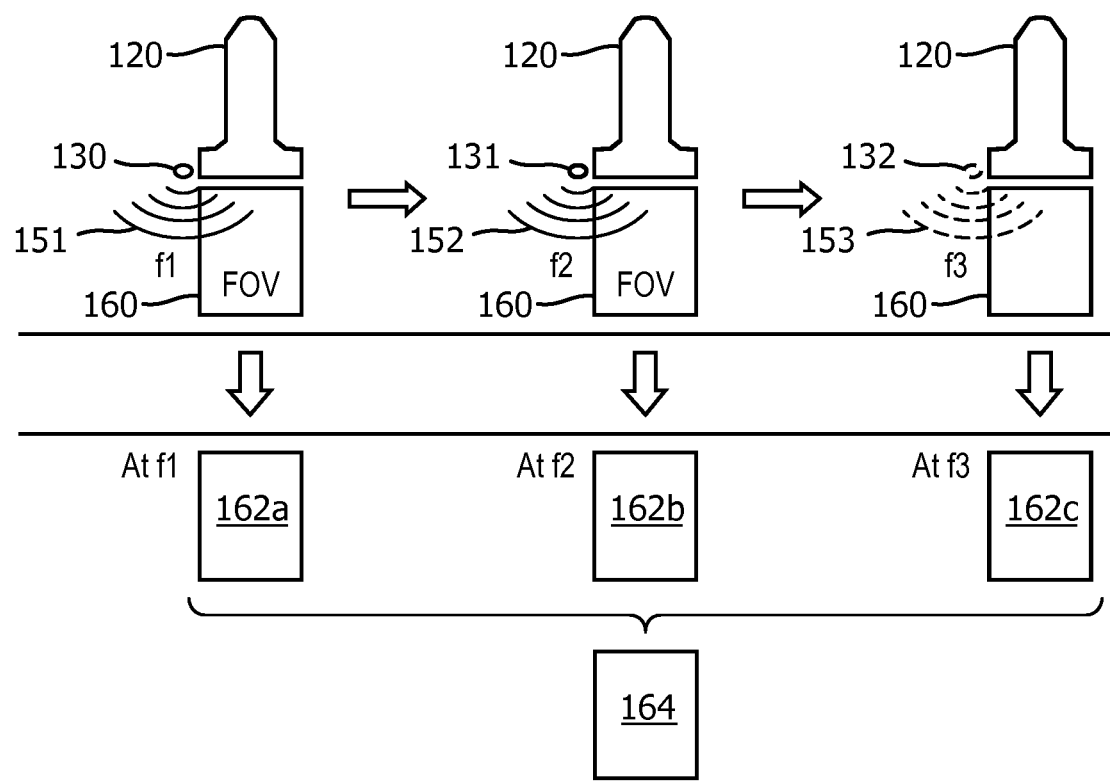
FIG. 12 is a diagrammatic view of an ultrasonic imaging system configured to determine the viscosity of an anatomy, according to aspects of the present disclosure.

FIG. 12 is an exemplary illustration of a shear wave ultrasound device 120 shown inducing a first shear wave 151, a second shear wave 152, and a third shear wave 153 in an anatomy, according to embodiments of the present disclosure. The device 120 may be similar or identical to the device 120 shown in FIG. 5. In the embodiment of FIG. 12, the device 120 further induces the third shear wave 153 at a third frequency f3, in addition to the first and second shear waves 151, 152. The first, second, and third shear waves 151, 152, 153, may be induced by a single vibration source 130, or each of the first, second, and third shear waves 151, 152, 153, may be induced by separate vibrations sources. The first, second, and third shear waves 151, 152, 153 may be induced at separate times, or one or more of the first, second, and third shear waves 151, 152, 153 can be induced at the same time. In an exemplary embodiment, the first, second, and third shear waves 151, 152, 153 are induced sequentially by the same vibration source 130. In the embodiment of FIG. 12, the second frequency f2 is greater than the first frequency f1, and the third frequency f3 is greater than the second frequency C. However, any suitable order or arrangement of frequencies f1, f2, f3 are contemplated by the present disclosure, including ascending or descending frequencies.

The imaging system of FIG. 12 is further configured to detect the third shear wave 153, in addition to the first and second shear waves 151, 152, and to determine a third wave speed of the third shear wave 153. The imaging system can obtain ultrasound data representative of the anatomy exhibiting the third shear wave 153 in a field of view 160. By determining the third wave speed at a plurality of locations in the field of view 160, the imaging system can be configured to compile or generate a third wave speed map 162c. The third wave speed map 162c can be compared to the first and/or second wave speed maps 162a, 162b and normalized by the frequency difference to determine the viscosity of the tissue. By inducing a third shear wave 153 and determining the third wave speed, the system may improve one or more aspects of determining the viscosity of the anatomy, such as an improvement in signal-to-noise ratio (SNR) and/or more accuracy in individual viscosity measurements.

Figure 13:
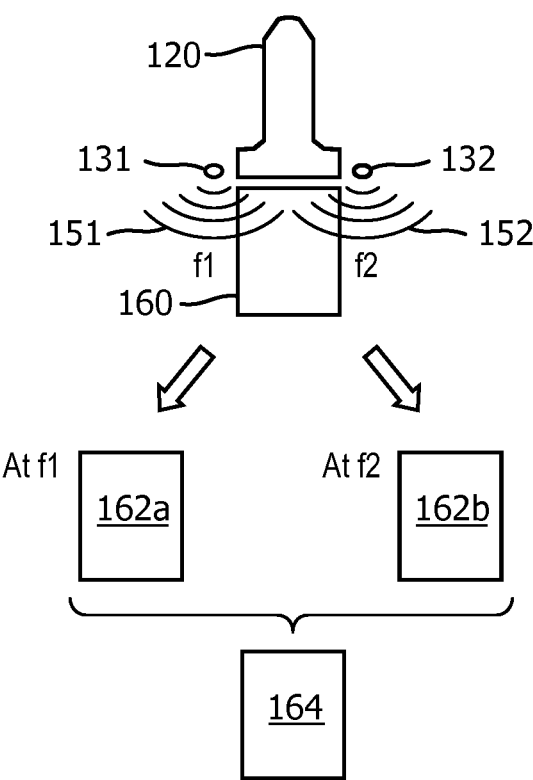
FIG. 13 is a diagrammatic view of an ultrasonic imaging system comprising two vibrators and configured to determine the viscosity of an anatomy, according to aspects of the present disclosure.

FIG. 13 shows a shear wave ultrasound device 120 of a shear wave imaging system inducing a first shear wave 151 and a second shear wave 152, according to some embodiments of the present disclosure. In the embodiment of FIG. 13, the device 120 includes a first vibration source 131 and a second vibration source 132. In some aspects, the device 120 can also be described as including a single vibration source comprising a first vibrator 131 and a second vibrator 132. In the illustrated embodiment, the device 120 is shown inducing the first shear wave 151 at a first frequency f1 via the first vibrator, or vibration source 131, and inducing the second shear wave 152 at a second frequency f2 via the second vibrator, or vibration source 132. In some embodiments, the device is configured to induce the first and second shear waves simultaneously via the first and second vibrators 131, 132. By inducing the first and second shear waves simultaneously, the system can reduce acquisition time for each viscosity map. In such embodiments, the system is configured to obtain ultrasonic data representative of the anatomy exhibiting the first and second shear waves 151, 152 in the field of view 160. If the first and second shear wave are simultaneously propagating, or traveling through the field of view 160, the imaging system can be configured to apply a directional filter to the obtained ultrasonic data in order to detect the first shear wave and the second shear wave. After applying the directional filter to the ultrasound data to detect the first and second shear waves 151, 152, the system can determine a first wave speed and a second wave speed associated with the first and second shear waves for a plurality of locations within the field of view. The system can then generate a first wave speed map and a second wave speed map representative of the first and second wave speeds of the first and second shear waves at each location in the field of view 160 (e.g., each pixel in the field of view). The first and second maps can be compared by, for example, subtracting the wave speeds of the second map from the wave speeds of the first map, and normalizing each wave speed by the difference of the first frequency and the second frequency.

It will be understood that although the device 120 is shown inducing shear waves at different frequencies f1 and f2, in other embodiments, the device 120 of FIG. 13 can be configured such that both vibrators induce a shear wave at the same frequency, or range of frequencies. For example, both vibrators 131, 132, can be configured to induce the first shear wave at the first frequency at a first time, and to induce the second shear wave at the second frequency at a second time. Such a configuration may improve SNR, and may at least partially resolve biased attenuation of the shear wave traveling across the field of view 160. For example, a shear wave induced by the first vibrator 131 may experience increased attenuation at the bottom right corner of the field of view as compared with the bottom left corner. By simultaneously activating the second vibrator 132 to induce the shear wave, the signal and/or attenuation of the wave can be more balanced across the field of view 160.

Figure 14:
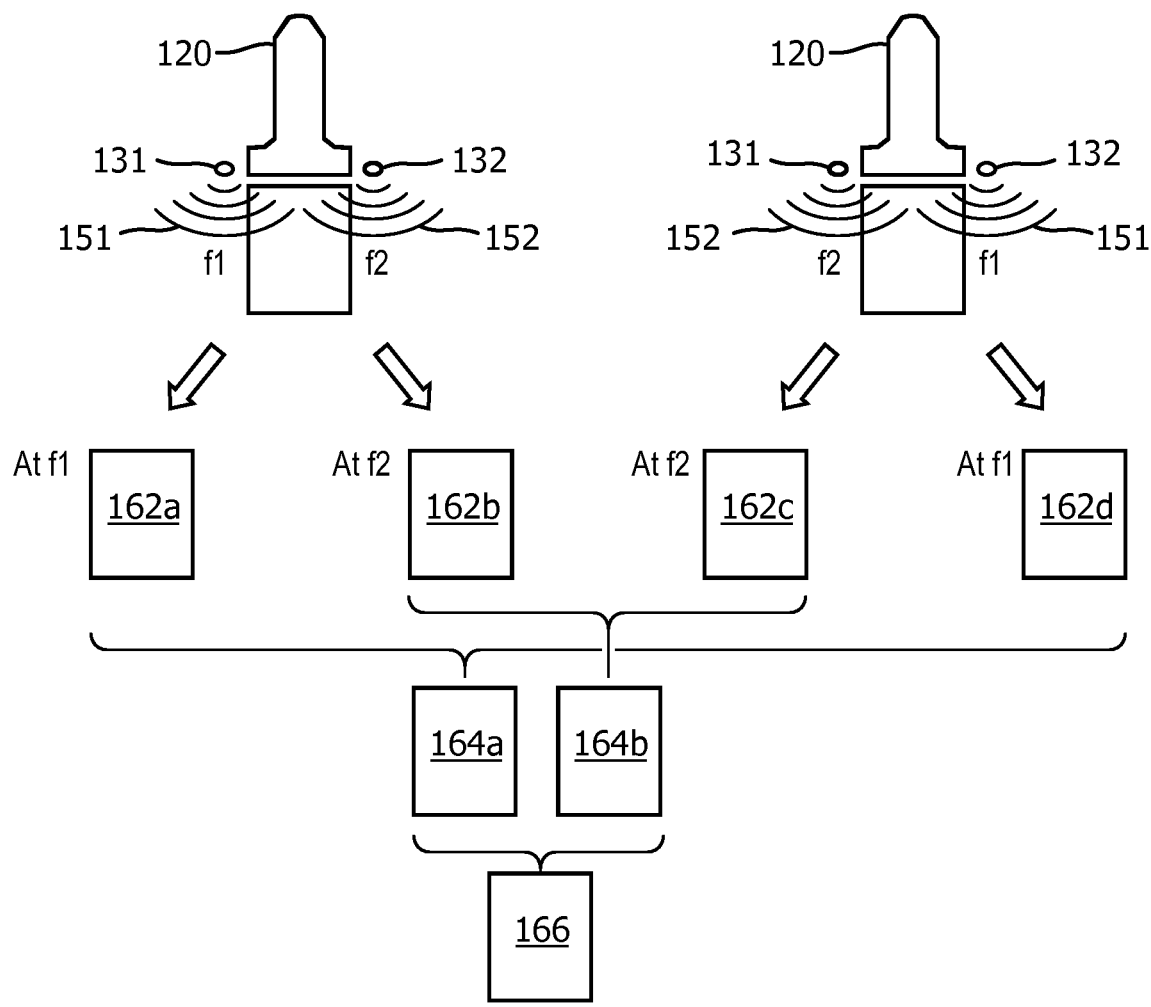
FIG. 14 is a diagrammatic view of an ultrasonic imaging system comprising two vibrators and configured to determine the viscosity of an anatomy, according to aspects of the present disclosure.

FIG. 14 depicts the shear wave ultrasound device 120 of FIG. 13, according to another embodiment of the present disclosure. In FIG. 14, the ultrasound device, including the first and second vibrator 131, 132, can be configured to induce a first and second shear wave, respectively, at a first time. The device 120 can then alternate the vibrators 131, 132 at a second time, such that the first vibrator 131 induces the second shear wave 152 at the second frequency f2, and the second vibrator 132 induces the first shear wave 151 at the first frequency f1. Although the first vibrator 131 is said to induce the first shear wave 151 at the first time, and the second shear wave 152 at the second time, the first shear wave 151 induced by the second vibrator 132 at the second time can alternatively be referred to as a third shear wave. Likewise, the second shear wave 152 induced by the first vibrator 131 at the second time can be referred to as a fourth shear wave.

As described above with respect to FIG. 13, when the first and/or second shear waves 151, 152 propagate diagonally across the field of view 160, the displacement or strength of the shear waves 151, 152 attenuates from left to right, and vice versa. One solution discussed above is to activate both vibrators 131, 132 to induce shear waves at the same frequency. The embodiment of FIG. 14 proposes another solution, which includes alternating the vibrators 131, 132 to induce shear waves at the first and second frequencies f1, f2 at different times. Such a configuration may also improve SNR and compensate for biased attenuation of signals.

Referring to FIG. 14, at the first time, the system obtains ultrasound data, and applies a directional filter to individually detect the first and second shear waves 151, 152. The ultrasound data is used to generate a first wave speed map 162a and a second wave speed map 162b. At the second time, wherein the vibrators 131, 132 have alternated to induce the second shear wave 152 and the first shear wave 151, the system obtains additional ultrasound data and applies a directional filter to individually detect the first and second shear waves 151, 152 (or fourth and third shear waves, respectively). The ultrasound data obtained at the second time is used to generate a third wave speed map 162c and a fourth wave speed map 162d. The first and fourth wave speed maps 162a, 162d associated with the first frequency f1 can then be combined by, e.g., averaging the individual values of the first and fourth wave speed maps 162a, 162d to create a first combined wave speed map 164a for frequency f1. The second and third wave speed maps 162b, 162c are also combined to produce a second combined wave speed map 164b associated with the second frequency C. The first and second combined wave speed maps 164a, 164b, having better SNR compared to individual speed maps 162a-162d at two different frequencies f1 and f2 can then be used to create a viscosity map 166 as described previously.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system for determining a viscosity of an anatomy, comprising:
 an ultrasound transducer;
 a vibration source;
 a display; and
 a processing system in communication with the ultrasound transducer, the vibration source, and the display, wherein the processing system is configured to:
  activate the vibration source to emit a broadband vibration and thereby induce a broadband shearwave propagating at a plurality of frequencies in the anatomy;
  activate the ultrasound transducer to obtain ultrasound data representative of the anatomy that exhibits the broadband shearwave;
  apply a band pass filter to the ultrasound data to identify:
   a first component of the broadband shear wave propagating at a first frequency of the plurality of frequencies; and
   a second component of the broadband shear wave propagating at a second frequency of the plurality of frequencies;
  determine a first wave speed of the first component in the anatomy and a second wave speed of the second component in the anatomy;

determine, based on comparison of the first wave speed and the second wave speed, the viscosity of the anatomy at a plurality of points in a field of view of the anatomy;

generate a visual depiction associated with the viscosity of the anatomy at each of the plurality of points in the field of view; and output, to the display, a screen display comprising an ultrasound image of the anatomy, the visual depiction, and a viscosity plot, wherein the ultrasound image and the viscosity plot are simultaneously displayed in the screen display, wherein the viscosity plot and the ultrasound image are separate from one another in the screen display, and wherein the viscosity plot comprises a first axis representative of a plurality of frequencies and a second axis representative of a plurality of wave speeds, wherein a first location in the viscosity plot corresponds to the first frequency along the first axis and the first wave speed along the second axis, and wherein a second location in the viscosity plot corresponds to the second frequency along the first axis and the second wave speed along the second axis.

2. The system of claim 1, wherein the processing system is configured to apply a directional filter to the obtained ultrasound data to generate direction-filtered ultrasound data, wherein the band pass filter is applied to the direction-filtered ultrasound data.

3. The system of claim 1, wherein the processing system is configured to:

activate the ultrasound transducer to obtain ultrasound imaging data of the anatomy; and generate the ultrasound image of the anatomy based on the obtained ultrasound imaging data; and wherein the visual depiction is overlaid on the ultrasound image in the screen display.

4. The system of claim 3, wherein the visual depiction comprises a map representative of the viscosity within the field of view.

5. The system of claim 1, wherein the processing system is configured to:

identify a third component of the broadband shearwave propagating at a third frequency of the plurality of frequencies;

determine a third wave speed of the third component; and determine the viscosity of the anatomy by comparing the first wave speed, the second wave speed, and the third wave speed, wherein a third location in the viscosity plot corresponds to the third frequency along the first axis and the third wave speed along the second axis.

6. A method for determining a viscosity of an anatomy, comprising:

inducing, by a vibration source, a broadband vibration and thereby induce a broadband shear wave in the anatomy propagating at a plurality of frequencies in the anatomy;

obtaining, by an ultrasound transducer, ultrasound data representative of the anatomy that exhibits the broadband shearwave;

applying a band pass filter to the ultrasound data and to identify:

a first component of the broadband shear wave propagating at a first frequency of the plurality of frequencies; and a second component of the broadband shear wave propagating at a second frequency of the plurality of frequencies;

determining, by a processing system in communication with the vibration source and the ultrasound transducer, a first wave speed of the first component in the anatomy and a second wave speed of the second component in the anatomy based on the obtained ultrasound data;

determining, by the processing system, the viscosity of the anatomy at a plurality of points in a field of view of the anatomy by comparing the first wave speed and the second wave speed;

generating, by the processing system, a visual depiction associated with the viscosity of the anatomy at each of the plurality of points in the field of view; and providing, on a display, a screen display comprising an ultrasound image of the anatomy, the visual depiction, and a viscosity plot, wherein the ultrasound image and the viscosity plot are simultaneously displayed in the screen display, wherein the viscosity plot and the ultrasound image are separate from one another in the screen display, and wherein the viscosity plot comprises a first axis representative of a plurality of frequencies and a second axis representative of a plurality of wave speeds, wherein a first location in the viscosity plot corresponds to the first frequency along the first axis and the first wave speed along the second axis, and wherein a second location in the viscosity plot corresponds to the second frequency along the first axis and the second wave speed along the second axis.

7. The method of claim 6, further comprising:

obtaining, by the ultrasound transducer, ultrasound imaging data of the anatomy; and generating, by the processing system, the ultrasound image of the anatomy based on the obtained ultrasound imaging data; and wherein the visual depiction is overlaid on the ultrasound image in the screen display.

8. The system of claim 3, wherein the visual depiction is overlaid on only a portion of the ultrasound image such that each pixel in the portion of the ultrasound image is associated with a viscosity value of a plurality of viscosity values.

9. The system of claim 8, wherein each pixel in the portion of the ultrasound image comprises a color of a plurality of colors corresponding to the associated viscosity value.

10. The system of claim 9, wherein the screen display further comprises a scale identifying a relationship between the plurality of colors and the plurality of viscosity values.

11. A system for determining a viscosity of an anatomy, comprising:

a processing system in communication with an ultrasound transducer and a display, wherein the processing system is configured to:

activate the ultrasound transducer to obtain ultrasound data representative of the anatomy exhibiting one or more shear waves apply a band pass filter to the ultrasound data to identify:

a first component of the one or more shear waves propagating at a first frequency; and a second component of the one or more shear waves propagating at a second frequency;

determine a first wave speed of the first component in the anatomy and a second wave speed of the second component in the anatomy;

determine, based on comparison of the first wave speed and the second wave speed, the viscosity of the anatomy at a plurality of points in a field of view of the anatomy;

generate a visual depiction associated with the viscosity of the anatomy at each of the plurality of points in the field of view; and output, to the display, a screen display comprising an ultrasound image of the anatomy, the visual depiction, and a viscosity plot, wherein the ultrasound image and the viscosity plot are simultaneously displayed in the screen display, wherein the viscosity plot and the ultrasound image are separate from one another in the screen display, and wherein the viscosity plot comprises a first axis representative of a plurality of frequencies and a second axis representative of a plurality of wave speeds, wherein a first location in the viscosity plot corresponds to the first frequency along the first axis and the first wave speed along the second axis, and wherein a second location in the viscosity plot corresponds to the second frequency along the first axis and the second wave speed along the second axis.

* * * * *